United States Patent [19]

Neidleman et al.

[11] Patent Number: 4,546,080
[45] Date of Patent: Oct. 8, 1985

[54] MANUFACTURE OF HALOGENATED KETONES AND ALDEHYDES

[75] Inventors: Saul L. Neidleman, Oakland; John Geigert, Clayton, both of Calif.

[73] Assignee: Cetus Corporation, Emeryville, Calif.

[21] Appl. No.: 229,554

[22] Filed: Jan. 29, 1981

[51] Int. Cl.[4] .................... C12P 7/26; C12P 7/24; C12M 1/40

[52] U.S. Cl. .................. 435/148; 435/147; 435/813; 435/288

[58] Field of Search ............ 435/147, 148, 149, 813, 435/288

[56] References Cited

U.S. PATENT DOCUMENTS

| | | | |
|---|---|---|---|
| 2,452,154 | 10/1948 | Ross et al. | 260/593 |
| 2,752,341 | 6/1956 | Magerlein | 260/239.55 |
| 3,277,187 | 10/1966 | Dewhirst | 260/633 |
| 4,024,193 | 5/1977 | Kruse | 260/618 D |
| 4,067,886 | 1/1978 | Reardon, Jr. et al. | 260/340.7 |
| 4,107,210 | 8/1978 | Freiter | 260/590 |
| 4,247,641 | 1/1981 | Neidleman et al. | 435/123 |
| 4,247,641 | 1/1978 | Neidleman et al. | 435/123 |
| 4,284,723 | 8/1981 | Neidleman et al. | 435/123 |

OTHER PUBLICATIONS

Morrison et al, *Organic Chemistry*, 2nd Ed. Allyn and Bacon Inc, (1969) p. 177-179, 195-198, 185-188, 201-203, and 249-250.

Hager, "Iodination of Tyrosine by Chloroperoxidase; Preparation of Chloroperoxidase". *Methods In Enzymology* vol. 42A, (1970) p. 648-652.

Hollemberg et al. "The Reaction Of Chlorite With Horseradish Peroxidase And Chloroperoxidase" *Journal Of Biological Chemistry* (1974) vol. 249(18) p. 5816-5825.

Walsh, *Enzymatic Reaction Mechanisms* W. H. Freeman and Co. (1979) p. 494-495.

Hallenberg et al. "Purification Of Chloroperoxidase From Caldariomyces Fum go" *Methods In Enzymology* vol. 52C (1978) p. 521-529.

Lowell P. Hager et al., Chemistry of Peroxidase Intermediates Ann. N.Y. Acad. Sci., vol. 288 (1975) pp. 80-93.

Richard Theiler et al., Halohydrocarbon Synthesis by Bromoperoxidase Science, vol. 202, Dec. 1978 pp. 1094-1096.

D. T. Downing et al., Structural Requirements of Acetylenic Fatty Acids for Inhibition of Soybean Lipoxygenase and Prostaglandin Synthetase, Biochim. Biophys. Acta 280 (1972) pp. 343-347.

Mitsuru Imuta, et al., Product Stereospecificity in the Microbial Reduction of $\alpha$-Haloaryl Ketones, J. Org. Chem. 1980 45, 3352-3355.

John Colby et al., The Soluble Methane Mono-oxygenase of *Methylococcus capsulatus* (Bath) Biochem. J. (1977) 165, 395-402.

Jerry March, "Reactions, Mechanisms, and Structure" in Advanced Organic Chemistry, McGraw-Hill pp. 991-995.

Louis F. Fieser et al. "Acetylenic Hydrocarbons" in Organic Chemistry, Pub. 1944 D. C. Heath & Company Boston pp. 75-83.

Saul Patai, The Chemistry of the Carbon-Carbon Triple Bond Part 1, 243 (1978).

Samuel F. Reed, "The Preparation of a, a-Dichloro Ketones" J. Org. Chem., 30:2195-2198 (1965).

Abeles et al., *J. Amer. Chem. Soc.* 95:6124-6125 (1973).

John D. Roberts and Marjorie C. Caserio, "Of Organic Chemistry" (1964) pp. 208-223.

*Primary Examiner*—Thomas G. Wiseman
*Assistant Examiner*—J. E. Tarcza
*Attorney, Agent, or Firm*—Albert P. Halluin; Janet E. Hasak

[57] ABSTRACT

A method is described for the manufacture of commercially useful alpha-halo and alpha-dihalo ketones and aldehydes from alkynes by enzymatic reaction. The alkyne is acted upon in a reaction mixture comprising a halogenating enzyme, an oxidizing agent, and a halide ion source.

11 Claims, No Drawings

MANUFACTURE OF HALOGENATED KETONES AND ALDEHYDES

This invention relates generally to the manufacture of alpha-halogenated ketones and aldehydes from alkynes. More particularly, the invention relates to an improved method for effecting this reaction enzymatically.

Alpha-halogenated ketones and aldehydes are commercially useful chemical intermediates and end-products in the manufacture of pharmaceuticals, dyestuffs and perfumes. For example, alpha-chloro acetaldehyde (I) is used in the manufacture of thyroid inhibitors. Alpha-bromo acetophenone (II) is a principal ingredient in nerve control gases.

$$\underset{(I)}{CH_2-\overset{\overset{\displaystyle Cl}{|}}{\underset{\underset{\displaystyle O}{\|}}{C}}H} \quad \underset{(II)}{CH_2-\overset{\overset{\displaystyle Br}{|}}{\underset{\underset{\displaystyle O}{\|}}{C}}-\phi}$$

These types of compounds serve as precursors for the synthetically important Favorski rearrangement which produces esters and alpha, beta-unsaturated esters (March, *Advanced Organic Chemistry*, 2nd Edition (1977)). U.S. Pat. No. 4,107,210 (Freiter, 1978) describes the preparation of alpha-diketones from alpha-halo ketones. In addition, the teaching of two other patents permits the manufacture of commercially important epoxides and glycols from these types of compounds. U.S. Pat. No. 3,277,187 (Dewhirst, 1966) and U.S. Pat. No. 4,024,193 (Kruse, 1977) describe the preparation of alpha, beta halohydrins from alpha-halo ketones using molecular hydrogen and a ruthenium catalyst. The alpha, beta halohydrins are then readily converted by base addition to epoxides, and then glycols.

The preparation of these useful halogenated compounds has involved processes reacting free halogen with either ketones and aldehydes or enol acylates.

$$X_2 + H_2O \longrightarrow \begin{cases} R'-CH_2-\overset{\overset{\displaystyle O}{\|}}{C}R \xrightarrow{\text{(Ross, U.S. Pat. No. 2,452,154 (1948))}} R'-\overset{\overset{\displaystyle X}{|}}{C}H-\overset{\overset{\displaystyle O}{\|}}{C}R + R'-\overset{\overset{\displaystyle X}{|}}{\underset{\underset{\displaystyle X}{|}}{C}}-\overset{\overset{\displaystyle O}{\|}}{C}R \\ R'-CH=\overset{\overset{\displaystyle OAc}{|}}{C}-R'' \xrightarrow{} R'-\overset{\overset{\displaystyle X}{|}}{C}H-\overset{\overset{\displaystyle O}{\|}}{C}-R'' \end{cases}$$

(Magerlein, U.S. Pat. No. 2,752,341 (1956))

where
$X_2$ = chlorine or bromine
R, R', R'' = hydrogen or hydrocarbon

In both methods of preparation, free halogen is handled. Free halogen requires expensive control procedures and equipment to prevent loss of this toxic, corrosive reactant. Also, free halogen is generally costly because of the energy-intensive processes employed for its production.

In methods using ketones and aldehydes as substrates, it is difficult to control the ratio of alpha-dihalo product to alpha-halo product (Reardon et al., U.S. Pat. No. 4,067,886 (1978)). In methods using enol acylate as a substrate, the cost of the enol acylate is a major objection.

Halogenated ketones and aldehydes have been prepared from alkynes (Reed, *J. Org. Chem.*, 30:2195–2198 (1965); Patai, *Chemistry of the Carbon-Carbon Triple Bond*, Part 1, 243 (1978)). Alkynes, particularly acetylene, are readily produced from coal and, as oil prices continue to rise, offer a highly interesting substrate for conversion to halogenated ketones and aldehydes. However, up to the present, typical methods of converting alkynes to such halogenated compounds use free halogen, thus requiring expensive control procedures and equipment as mentioned above. In addition, these methods produce only the alpha-dihalo products and none of the alpha-halo products.

$$RC\equiv CH \xrightarrow[H_2O]{X_2} RC\overset{\overset{\displaystyle O}{\|}}{\underset{\underset{\displaystyle X}{\diagdown}}{-}}\overset{\overset{\displaystyle X}{\diagup}}{C}H$$

where
R = hydrocarbon
$X_2$ = chlorine or bromine.

Accordingly, it is an object of the present invention to provide a process for preparing both the alpha-halo and the alpha-dihalo ketones and aldeydes.

It is also an object of the present invention to prepare these compounds without using free halogen.

Another object of the present invention is to provide such a process that permits control of the ratio of alpha-halo product to alpha-dihalo product.

It is a further object of the present invention to provide a low cost process for producing the desired products from alkynes.

Other objects will become apparent to those skilled in the art from the following description.

Very generally, the method of the invention produces alpha-halo and alpha-dihalo ketones and aldehydes from alkynes by providing in a reaction vessel a reaction mixture of a halogenating enzyme, an oxidizing agent and a halide ion source. An alkyne is introduced into the reaction vessel and maintained in contact with the reaction mixture for a sufficient period of time to convert the alkyne to the desired ketone or aldehyde or a mixture of both.

The present invention is based on the discovery that the group of enzymes classified as haloperoxidases acts upon alkynes (i.e., carbon-carbon triple bonds) to produce alpha-halo and alpha-dihalo ketones and aldehydes. These products are characterized by the structural formula:

$$-\overset{\displaystyle }{\underset{\displaystyle }{C}}-\overset{\overset{\displaystyle O}{\|}}{\underset{\underset{\displaystyle }{}}{C}}-\overset{\overset{\displaystyle X}{|}}{\underset{\underset{\displaystyle }{}}{C}}- \quad -\overset{\displaystyle }{\underset{\displaystyle }{C}}-\overset{\overset{\displaystyle O}{\|}}{\underset{\underset{\displaystyle }{}}{C}}-\overset{\overset{\displaystyle X}{|}}{\underset{\underset{\displaystyle }{}}{C}}- \quad -\overset{\overset{\displaystyle X}{|}}{\underset{\underset{\displaystyle X}{|}}{C}}-\overset{\overset{\displaystyle O}{\|}}{\underset{\underset{\displaystyle }{}}{C}}-\overset{\overset{\displaystyle X}{|}}{\underset{\underset{\displaystyle }{}}{C}}-$$

where X is selected from a group consisting of chloride, bromide or iodide. Although it is known that haloperoxidases act upon active methylene or methine groups (Theiler et al., *Science*, 202:1096–1097 (1978); Hager et al., *Ann. N.Y. Acad. Sci.* 244:80–93 (1975)) and although it is known that haloperoxidases act upon carbon-carbon double bonds (Neidleman et al., U.S. Pat. No. 4,247,641), it is not known that haloperoxidases act upon carbon-carbon triple bonds.

It is surprising that alkynes can serve as suitable substrates for this group of enzymes. Alkyne substrates are generally regarded as enzyme inactivators (Abeles et al., *J. Amer. Chem. Soc.*, 95:6124–6125 (1973)). For example, the oxidation of gaseous alkenes such as ethylene and propylene by the methane mono-oxygenase enzyme is inhibited by the addition of gaseous alkynes such as acetylene to the reaction (Colby et al., *Biochem. J.*, 165:395–402 (1977)); and the oxidation of linoleic acid by soybean lipoxygenase is irreversibly inhibited when carbon-carbon triple bonds are substituted for the carbon-carbon double bonds (Downing et al., *Biochem. Biophys. Acta*, 280:343–347 (1972)).

The aforementioned U.S. Pat. No. 4,247,641 (Neidleman et al.) describes the preparation of epoxides and glycols from the alpha-halohydrins using an enzymatic process.

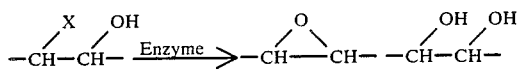

where x=chloride, bromide or iodide.

Halohydrins, and the resulting epoxides, produced from alkenes by haloperoxidase as described in the Neidleman et al. patent, above, are not optically active. However, halo-hydrins and the resulting epoxides produced from alkynes can be optically active. The key to this process involves the stereo-specific microbial reduction of the alpha-halo ketone intermediates:

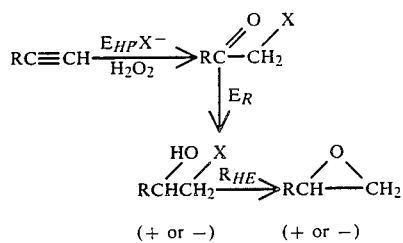

where
x=bromide, chloride or iodide,
$E_{HP}$=haloperoxidase,
$E_R$=reductase,
$E_{HE}$=halohydrin epoxidase, and
R=hydrocarbon or hydrogen.

A description of the action of a reductase ($E_R$) suitable for the foregoing process is described by Imuta et al., *J. Org. Chem.*, 45:3352–3355, (1980).

The alkynes useful in the process of the invention can be broadly defined as any hydrocarbon containing a carbon-to-carbon triple bond, represented by the following structural formula:

wherein each of $R_1$ and $R_2$ is selected from a group consisting of hydrogen and hydrocarbon. Representative alkynes are:

| Alkyne | $R_1$ | $R_2$ |
|---|---|---|
| acetylene | H | H |
| methyl acetylene | $CH_3$ | H |
| ethyl acetylene | $CH_3CH_2$ | H |
| phenyl acetylene | ∅ | H |
| 1-phenyl-1-propyne | ∅ | $CH_3$ |

The process of preparation comprises the introduction of an alkyne into a reaction mixture of a halogenating enzyme, a source of halide ion, and an oxidizing agent. The reaction proceeds spontaneously and rapidly under ambient conditions of temperature and pressure.

The present invention makes use of haloperoxidase enzymes. Such enzymes include chloroperoxidase derived from the microorganism *Caldariomyces fumago*, bromoperoxidase derived from seaweed, lactoperoxidase derived from milk, thyroid peroxidase derived from the thyroid, myeloperoxidase derived from leukocytes, and horseradish peroxidase derived from horseradish. Certain of these haloperoxidases are commercially available.

The preferred haloperoxidase depends upon the products desired. The halides that the given haloperoxidases can use are listed below:

| Haloperoxidase | Halides |
|---|---|
| myeloperoxidase | $Cl^-$, $Br^-$, $I^-$ |
| chloroperoxidase | $Cl^-$, $Br^-$, $I^-$ |
| lactoperoxidase | $Br^-$, $I^-$ |
| bromoperoxidase | $Br^-$, $I^-$ |
| thyroid peroxidase | $I^-$ |
| horseradish peroxidase | $I^-$ |

For ease of discussion, various aspects of the present invention will be described with particularity, but not exclusively, in connection with the use of the preferred peroxidase, chloroperoxidase, derived from *Caldariomyces fumago*. The microorganism, *Caldariomyces fumago*, may be grown as a static or agitated, submerged culture in Czapek-Dox medium at room temperature for 3 to 10 days by conventional methods. The halogenating enzyme, chloroperoxidase, is prepared from an aqueous homogenate of the mycelial pads of the microorganism grown under static conditions or from the filtrate of the microorganism grown under static or agitated submerged culture conditions.

The halogenating enzyme may also be used in an immobilized form. Processes for enzyme immobilization are familiar to those skilled in the art, and include reacting either a solution of the enzyme or a suspension of enzyme containing cells with one of a broad range of organic and inorganic supports. Included among these are polyacrylamide ethylene-maleic acid copolymers, methacrylic-based polymers, polypeptides, styrene-based polymers, agarose, cellulose, dextran, porous glass beads, and aluminum or titanium hydroxide. Enzymes in this form have increased stability, extended life and usefulness, and recoverability. Reactions employing immobilized enzymes may be run in columns or reaction tanks.

In addition to the halogenating enzyme, a source of inorganic halide and an oxidizing agent are required in the reaction mixture. A preferred oxidizing agent is hydrogen peroxide, which may be added directly to the mixture in a single batch addition, or in a continuous slow feed. It may alternatively be generated as a slow feed in situ by the use of a hydrogen peroxide-producing enzyme system. Such enzyme systems are well known in the art, and include glucose-1-oxidase in the presence of D-glucose, pyranose-2-oxidase or glucose-2-oxidase in the presence of D-glucose, D- and L-amino acid oxidases in the presence of D- and L-methionine, methanol oxidase in the presence of methanol, and diamine oxidases in the presence of histamine. The hydrogen peroxide-generating system may be present in the non-immobilized or immobilized state as with the halogenating enzyme. The hydrogen peroxide may also be generated by a chemical reaction, such as the anthraquinone or isopropyl alcohol oxidation processes.

The hydrogen peroxide is present preferably in a molar ratio of from about 0.5:1 to about 50:1, most preferably in a ratio of about 1:1 or less with respect to the alkyne. The molar ratio preferences refer to the average presence of hydrogen peroxide during the reaction. The actual molar ratio will usually vary during the reaction and the molar ratio at any particular time may be above or below the ranges cited. Other suitable oxidizing agents include organic peroxides, such as methyl, ethyl, or butyl peroxides.

The halogen source may be any of the water-soluble halide salts. The preferred halogen sources are the chloride, bromide, and iodide salts of the alkali metals, sodium and potassium. The salts are present in the reaction mixture at a level sufficient to provide a slight excess of halide ion with respect to the stoichiometric amount required for the reaction.

The reaction is conducted within the pH range of from about 2.2 to about 8.0. The pH of the reaction may be maintained within the desired range by use of a buffering agent. Suitable buffers include sodium or potassium phosphate based systems. Other suitable techniques besides buffering may be used for pH control and adjustment. The reaction is preferably conducted in an aqueous medium. While some of the alkynes that can be converted by the process are substantially insoluble in an aqueous medium, the reaction, nevertheless, occurs satisfactorily under conditions of mixing, or other modes of dispersion, which provide sufficient substrate solubility for the reaction.

It is also contemplated that the reaction can be conducted in the presence of low levels of organic solvents to increase substrate solubility. The reaction is preferably conducted under aerobic conditions and in the temperature range of 15° to about 50°, preferably about 20° to about 30°.

As previously indicated, the components of the reaction mixture, namely the alkyne, the halogenating enzyme, the oxidizing agent, the halide ion source, and the buffering agent, are simply mixed together in water or mixed aqueous or organic media, and agitated for a period of from about 30 seconds to about 1 hour to obtain the halogenated products. Lower linear alkynes, such as acetylene, methyl acetylene or ethyl acetylene, which are gaseous, can be reacted upon by simply passing the gaseous alkynes through the reaction mixture.

The control over the ratio of alpha-halo product to alpha-dihalo product is obtained by the choice of halide used and by the balance of available alkyne substrate and enzymatic activity. When chloride is the halide source, the alpha-dihalo product predominates. When iodide is the halide source, the alpha-halo product predominates. If the reaction is run under alkyne substrate-limiting conditions, the enzymatic reaction may proceed to convert the initial alpha-halo product into the alpha-dihalo product. Thus, by controlling the activity of the enzyme system relative to the availability of the alkyne substrate, control over product ratio is obtained. The level of enzymatic activity in the reaction mixture is controlled by the amount and intrinsic activity of the enzyme added, by the pH of the operation, and by the control over available hydrogen peroxide in the reaction mixture.

Analysis of the halogenated products is accomplished by gas chromatography (GC) using mass spectrometric detection. A 6-foot glass column packed with Tenax-GC, 80/100 mesh (Applied Sciences Lab., State College, Pa.), operated at 100° C. to 250° C. at 10° C./minute temperature programming, is attached to a Finnigan 4021 GCMS (Finnigan Corp. Sunnyvale, Ca.). Detection, quantitation and structure identification are made possible by operating the mass spectrometer (MS) at 70 eV electron impact ionization. Reaction mixtures are analyzed by direct injection (10 $\mu$l) of the aqueous reaction mixtures and by ethyl ether extraction, concentration and then injection.

The following examples are intended only to further illustrate the invention and are not intended to limit the scope of the invention which is defined by the claims.

Example 1

Potassium bromide (50 mg) and potassium phosphate buffer (8 ml 0.1 M, pH 3.0) were mixed together in a 100 ml Pyrex flask at room temperature and room pressure. The gaseous alkyne, methyl acetylene, was continuously bubbled into the mixture. The haloperoxidase enzyme, chloroperoxidase (0.1 ml), was added, followed by addition of dilute hydrogen peroxide (0.4 ml of 3% solution). The reaction was concluded 30 minutes after the addition of this last reagent.

The chloroperoxidase was prepared as follows:

Mycelial pads of *Caldariomyces fumago* (ATCC 16373) were grown on potato agar slants. Sliced potato (200 g) was cooked in distilled water (500 ml) for 40 minutes and then strained. A solution of glucose (21 g) and agar (20 g) in distilled water (500 ml) was added to the strained solution. The pH was adjusted to 6.8 and the volume was brought to 1 liter with distilled water. The medium was sterilized at 121° for 15 minutes.

The organism was inoculated on the potato agar slants, produced in accordance with the above procedure, and was grown for about one week at room temperature. The organism was then used to inoculate a soybean-glucose medium (50 ml). The soybean-glucose medium was prepared by adding, to 1 liter of distilled water, extraction process soybean meal (30 g), glucose (30 g), and $CaCO_3$ (7 g). The medium was sterilized at 121° for 30 minutes and was then inoculated with the organism after cooling.

The organism was grown for 4–5 days on a rotary shaker at 25°. 5 ml of this material was used in inoculate a 500 ml Erlenmeyer flask containing 100 ml of a modified Czapek-Dox medium prepared by adding the following to 1 liter of distilled water: $NaNO_3$ (3 g), $KH_2PO_4$ (1 g), KCl (0.5 g), $MgSO_4.7H_2O$ (0.5 g), $FeSO_4.7H_2O$ (10 mg) and glucose (40 g). The medium was sterilized at 121° for 20 minutes prior to inoculation with the organism.

The organism was grown under static conditions at room temperature 5–7 days. The black mycelial pads which formed were collected, rinsed with distilled water, and stored in plastic bags in a freezer at $-10°$ for subsequent use.

The halogenating enzyme was prepared by grinding 6 mycelial pads (prepared in accordance with the above procedures) with 60 g acid-washed sand and 60 ml distilled water for 2 minutes in a Virtis 45 homogenizer. The homogenate was centrifuged while cold and the supernatant solution was used as the source of the halogenating enzyme, chloroperoxidase.

The final chloroperoxidase supernatant was filtered through Whatman No. 1 paper at room temperature. The filtrate was concentrated about 10-fold using a rotary film evaporator at reduced pressure and temperature <35°. The concentrate was chilled to 0° in an ice bath, and pre-chilled (0°) ethanol was added until 45% ethanol (v/v) was reached. The mixture was stirred vigorously for 15 minutes, and then centrifuged at −10° (at 15,000 g) with a 55-34 rotor in a Sorval RC-5 Superspeed for 15 minutes. The black sediment was discarded. To the centrifugate, cooled at 0°, was added additional prechilled ethanol to give 65% ethanol (v/v). The mixture was slowly stirred for 30 minutes at 0°, and then centrifuged as before. The centrifugate was discarded, and the precipitate containing the chloroperoxidase activity was dissolved in 1 ml of 0.05 M potassium phosphate buffer (pH 7). The enzyme solution was stored at −20°.

The products were detected and identified by gas chromatography-mass spectrometry (GCMS). The reaction mixtures were extracted with ethyl ether (3×5 ml volumes). The ethyl ether layer was separated and then taken down to a 1 ml volume by blowing nitrogen over it at 40° C. 10 μl of this concentrated extract was injected into a Finnigan 4021 GCMS, equipped with a 6 foot by ¼ inch coiled, glass column, packed with Tenax-GC (80/100 mesh). Flow rate through the column was set as 30 ml per minute; the column temperature was programmed from 100° C. to 250° C. at a rate of 10° C./minute; the mass spectrometer was set at 70 eV electron impact ionization.

Four products were detected.

The major product had a GC retention time of 10 minutes and showed the mass spectrum diagnostic for bromoacetone: Molecular mass ion at mass 136 and 138 (1:1 in intensity), indicating 1 bromine atom on the molecule; major fragment mass ions at mass 57 for loss of a bromine atom from the molecular ion, at mass 79 and 81 (1:1 in intensity) for $Br^+$·ion, and at mass 93 and 95 (1:1 in intensity) for $CH_2Br^{1+}$·ion.

A second product had a GC retention time of 13 minutes and showed the mass spectrum diagnostic for 1,1-dibromoacetone: molecular mass ion at mass 214, 216 and 218 (1:2:1 in intensity), indicating 2 bromine atoms on the molecule; major fragment mass ions at mass 43 for $CH_3C\equiv O^+$ ion, at mass 79 and 81 (1:1 in intensity) for $Br^+$·ion, at mass 135 and 137 (1:1 in intensity) for loss of a bromine atom from the molecular ion, and at mass 171, 173 and 175 (1:2:1 in intensity) for $CHBr_2^{1+}$·ion.

A minor product had a GC retention time of 15 minutes and showed the mass spectrum diagnostic for 1,3-dibromoacetone:molecular mass ion at mass 214, 216 and 218 (1:2:1 in intensity), indicating 2 bromine atoms on the molecule; major fragment mass ions at mass 79 and 81 (1:1 in intensity) $Br^+$·ion, at mass 93 and 95 (1:1 in intensity) for $CH_2Br^{1+}$·ion, and at mass 121 and 123 (1:1 in intensity) for $O^+\equiv CCH_2Br$ ion.

A second minor product had a GC retention time of 9 minutes and showed the mass spectrum diagnostic for 1-bromo-2-propanol: molecular mass ion at mass 138 and 140 (1:1 in intensity), indicating 1 bromine atom on the molecule; major fragment mass ions at mass 45 for $CH_3CH=OH^{1+}$·ion, at mass 79 and 81 (1:1 in intensity) for $Br^+$·ion, at mass 93 and 95 (1:1 in intensity) for $CH_2Br^{1+}$·ion and at mass 123 and 125 (1:1 in intensity) for loss of a methyl group from the molecular ion. This product had an identical GC retention time and mass spectrum with that of an authentic sample of 1-bromo-2-propanol (purchased from Pfaltz and Bauer Chemical Company). The source of this minor product was of enzymatic origin since this product was not detected in the reaction run without added chloroperoxidase. Also, the source of this minor product was from the alkyne since no propylene could be detected in the methyl acetylene (detection was by GCMS; at 40° C. on the 6 foot Tenax-GC column, a propylene standard eluted at 8 minutes while methyl acetylene eluted at 12 minutes retention time).

The following summarizes the products obtained:

| Product | % of Total Yield |
|---|---|
| $CH_3C(=O)-CH_2Br$ | 50 |
| $CH_3C(=O)-CHBr_2$ | 30 |
| $BrCH_2-C(=O)-CH_2Br$ | 15 |
| $CH_3CH(OH)-CH_2Br$ | 5 |
| | Total Yield = 18 mg |

EXAMPLE 2

The procedure of Example 1 was followed except that potassium chloride was substituted for potassium bromide.

Four products were detected.

The major product had a GC retention time of 10 minutes and showed the mass spectrum diagnostic for 1,1-dichloroacetone:molecular mass ion at mass 126,128 and 130 (5:4:1 in intensity), indicating 2 chlorine atoms on the molecule; major fragment mass ions at mass 43 for $CH_3C\equiv O^+$ ion and at mass 83,85 and 87 (5:4:1 in intensity) for $CHCl_2^+$·ion. The mass spectrum of this product had an identical mass spectrum with that of an authentic sample of 1,1-dichloroacetone found in the National Bureau of Standards NSRDS-NBS 63 MS reference library.

A minor product had a GC retention time of 8 minutes and showed the mass spectrum diagnostic for chloroacetone:molecular mass ion at mass 92 and 94 (3:1 in intensity), indicating 1 chlorine atom on the molecule; major fragment mass ion at mass 57 for loss of a chlorine atom from the molecular ion. This product had an identical GC retention time and mass spectrum with that of an authentic sample of chloroacetone (purchased from Aldrich Chemical Company).

A second minor product had a GC retention time of 12 minutes and showed the mass spectrum diagnostic for 1,3-dichloroacetone: molecular mass ion at mass 126,128 and 130 (5:4:1 in intensity), indicating 2 chlorine atoms on the molecule; major fragment_mass ions at mass 49 and 51 (3:1 in intensity) for $CH_2Cl^{1+}$·ion and at mass 77 and 79 (3:1 in intensity) for $O^+\equiv CCH_2Cl$ ion. The mass spectrum of this product had an identical mass spectrum with that of an authentic sample of 1,3-dichloroacetone found in the National Bureau of Standards NSRDS-NBS 63 MS reference library.

A third minor product had a GC retention time of 7 minutes and showed the mass spectrum diagnostic for 1-chloro-2-propanol:molecular mass ion at mass 94 and 96 (3:1 in intensity), indicating 1 chlorine atom on the molecule; major fragment mass ions at mass 45 for $CH_3CH=OH^{1+}$ ion, at mass 79 and 81 (3:1 in intensity) for loss of a methyl group from the molecular ion. This product had an identical GC retention time and mass spectrum with that of an authentic sample of 1-chloro-2-propanol (purchased from Aldrich Chemical Company).

The following summarizes the products obtained:

| Product | % of Total Yield |
|---|---|
| $CH_3\overset{O}{\overset{\|\|}{C}}-CH_2Cl$ | 8 |
| $CH_3\overset{O}{\overset{\|\|}{C}}-CHCl_2$ | 75 |
| $ClCH_2\overset{O}{\overset{\|\|}{C}}-CH_2Cl$ | 15 |
| $CH_3\overset{OH}{\overset{\|}{C}H}-CH_2Cl$ | 2 |
| Total Yield = 12 mg | |

EXAMPLE 3

The procedure of Example 1 was used except that potassium iodide was substituted for potassium bromide.

One product was detected.

This product had a GC retention time of 12 minutes and showed the mass spectrum diagnostic for iodoacetone: molecular mass ion at mass 184; major fragment mass ions at mass 57 for loss of an iodine atom from the molecular ion, at mass 127 for $I^{30}$ ion, and at mass 141 for $CH_2I^{1+}$ ion.

The following summarizes the products obtained:

| Product | % of Total Yield |
|---|---|
| $CH_3\overset{O}{\overset{\|\|}{C}}-CH_2I$ | ~100 |
| $CH_3\overset{O}{\overset{\|\|}{C}}-CHI_2$ | N.D. |
| $ICH_2\overset{O}{\overset{\|\|}{C}}-CH_2I$ | N.D. |
| $CH_3\overset{OH}{\overset{\|}{C}H}-CH_2I$ | N.D. |
| Total Yield = 6 mg | |

N.D. = not detected

Examples 1 through 3 demonstrate the control of the ratio of alpha-halo product to alpha-dihalo product using halide substrates. Iodide favors the formation of alpha-halo product (Example 3), while chloride favors the formation of alpha-dihalo product (Example 2).

EXAMPLE 4

This example demonstrates the control of the ratio of alpha-halo product to alpha-dihalo product by balancing the level of available alkyne substrate with the level of enzymatic activity. Enzymatic activity is controlled in this example by the pH of the reaction.

The procedure of Example 1 was followed. The feed of methyl acetylene was held identical and constant in two separate flasks. The buffer in one flask was set at pH 3.0 (the optimum pH for chloroperoxidase activity). The buffer in the other flask was set at pH 4.0 (chloroperoxidase is much less reactive at pH 4.0 than at pH 3.0).

The products and product ratios obtained were the following:

| Products | % of Total Yield | |
|---|---|---|
| | pH 3.0 | pH 4.0 |
| $CH_3\overset{O}{\overset{\|\|}{C}}-CH_2Br$ | 50 | 80 |
| $CH_3\overset{O}{\overset{\|\|}{C}}-CHBr_2$ | 30 | 10 |
| $BrCH_2\overset{O}{\overset{\|\|}{C}}-CH_2Br$ | 15 | 10 |
| $CH_3\overset{OH}{\overset{\|}{C}H}-CH_2Br$ | 5 | N.D. |
| Total Yield = 18 mg (pH 3.0) 5 mg (pH 4.0) | | |

N.D. = not detected

EXAMPLE 5

The procedure of Example 1 was used except ethyl acetylene was substituted for methyl acetylene.

Four products were detected.

The major product had a GC retention time of 14 minutes and showed the mass spectrum diagnostic for 1-bromo-2-butanone:molecular mass ion at mass 150 and 152 (1:1 in intensity), indicating 1 bromine atom on the molecule; major fragment mass ions at mass 71 for loss of a bromine atom from the molecular ion, at mass 79 and 81 (1:1 in intensity) for $Br^+$ ion and at mass 135 and 137 (1:1 in intensity) for loss of a methyl group from the molecular ion.

A second product had a GC retention time of 18 minutes and showed the mass spectrum diagnostic for 1,1-dibromo-2-butanone:molecular mass ion at mass 228, 230 and 232 (1:2:1 in intensity), indicating 2 bromine atoms on the molecule; major fragment mass ions as mass 79 and 81 (1:1 in intensity) for $Br^+$ ion, at mass 149 and 151 (1:1 in intensity) for a loss of a bromine atom from the molecular ion, and at mass 213, 215 and 217 (1:2:1 in intensity) for loss of a methyl group from the molecular ion.

A third product had a GC retention time of 21 minutes and showed the mass spectrum diagnostic for 1,3-dibromo-2-butanone:molecular mass ion at mass 228, 230 and 232 (1:2:1 in intensity), indicating 2 bromine atoms on the molecule; major fragment mass ions at mass 79 and 81 (1:1 in intensity) for $Br^+$ ion, at mass 149 and 151 (1:1 in intensity) for loss of a bromine atom from the mclecular ion, and at mass 213, 215 and 217 (1:2:1 in intensity) for loss of a methyl group from the molecular ion.

A minor product had a GC retention time of 13 minutes and showed the mass spectrum diagnostic for 1- bromo-2-butanol:molecular mass ion at mass 152 and 154 (1:1 in intensity), indicating 1 bromine atom on the molecule; major fragment mass ions at mass 59 for $CH_3CH_2CH=OH^{]+}$ion, at mass 79 and 81 (1:1 in intensity) for $Br^+\cdot$ion, at mass 93 and 95 (1:1 in intensity) for $CH_2Br^{]+}\cdot$ion, and at mass 123 and 125 (1:1 in intensity) for loss of an ethyl group from the molecular ion.

The following summarizes the products obtained:

| Product | % of Total Yield |
|---|---|
| $CH_3CH_2\overset{O}{\overset{\|}{C}}-CH_2Br$ | 40 |
| $CH_3CH_2\overset{O}{\overset{\|}{C}}-CHBr_2$ | 25 |
| $CH_3CHBr\overset{O}{\overset{\|}{C}}-CH_2Br$ | 25 |
| $CH_3CH_2\overset{OH}{\overset{\|}{C}H}-CH_2Br$ | 10 |
| Total Yield = 11 mg | |

EXAMPLE 6

The procedure of Example 1 was followed except that phenyl acetylene was substituted for methyl acetylene. Since phenyl acetylene is a liquid alkyne, it was added to the flask (0.05 ml) at the start rather than bubbled in.

Two products were detected.

The major product had a GC retention time of 18 minutes and showed the mass spectrum diagnostic for alpha,alpha-dibromoacetophenone:molecular mass ion at mass 276, 278 and 280 (1:2:1 in intensity), indicating 2 bromine atoms on the molecule; major fragment mass ions at mass 77 for $\phi^+\cdot$ion, at mass 105 for $O^+\equiv C-\phi$ ion, and at mass 171, 173 and 175 (1:2:1 in intensity) for $CHBr_2^{]+}\cdot$ion.

The minor product had a GC retention time of 15 minutes and showed the mass spectrum diagnostic for alpha-bromoacetophenone:molecular mass ion at mass 198 and 200 (1:1 in intensity), indicating 1 bromine atom on the molecule; major fragment mass ions at mass 77 for $\phi^+\cdot$, at mass 93 and 95 (1:1 in intensity) for $CH_2Br^{]+}\cdot$ion, and at mass 105 for $O^+\equiv C-\phi$ ion. This product had an identical GC retention time and mass spectrum with that of an authentic sample of alpha-bromoacetophenone (purchased from Aldrich Chemical Company).

The following summarizes the products obtained:

| Product | % of Total Yield |
|---|---|
| $\phi-\overset{O}{\overset{\|}{C}}-CH_2Br$ | 5 |
| $\phi-\overset{O}{\overset{\|}{C}}-CHBr_2$ | 95 |
| Total Yield = 23 mg | |

EXAMPLE 7

This example demonstrates the control of the ratio of alpha-halo product to alpha-dihalo product by balancing the level of available alkyne substrate with the level of enzymatic activity. Enzymatic activity is controlled in this example by the availability of hydrogen peroxide.

The procedure of Example 6 was followed in two reactions, except that lactoperoxidase (purchased from Sigma Chemical Company) was substituted for chloroperoxidase and the pH of the buffer was 6.0 instead of 3.0.

In the first reaction flask, direct addition of dilute hydrogen peroxide was made.

In the second reaction flask, in-situ generation of hydrogen peroxide was made by adding β-D-glucose (50 mg) and glucose-1-oxidase (0.01 ml; purchased from Sigma Chemical Company).

The products and product ratios obtained were the following:

| | % of Total Yield | |
|---|---|---|
| Products | Direct $H_2O_2$ Addition | In-situ $H_2O_2$ Generation |
| $\phi-\overset{O}{\overset{\|}{C}}-CH_2Br$ | 10 | 95 |
| $\phi-\overset{O}{\overset{\|}{C}}-CHBr_2$ | 90 | 5 |
| Total Yield = 12 mg (Direct) 21 mg (in-situ) | | |

EXAMPLE 8

The procedure of Example 6 was followed except that 1-phenyl-1-propyne was substituted for phenyl acetylene. Two products were detected. The major product had a GC retention time of 20 minutes and showed the mass spectrum diagnostic for alpha, alpha-dibromoethyl phenyl ketone:molecular mass ion at mass 290, 292 and 294 (1:2:1 in intensity), indicating 2 bromine atoms on the molecule; major fragment mass ions at mass 77 for $\phi^+\cdot$ion, at mass 105 for $O^+\equiv C-\phi$ ion, and at mass 183, 185, 187 (1:2:1 in intensity) for $C(Br)_2CH_3^{]+}\cdot$ion.

The minor product had a GC retention time of 17 minutes and showed the mass spectrum diagnostic for ε-bromoethyl phenyl ketone:molecular mass ion at mass 212 and 214 (1:1 in intensity), indicating 1 bromine atom on the molecule; major fragment mass ions at mass 77 for $\phi^+\cdot$ion and at mass 105 for $O^+\equiv C-\phi$ion. The following summarizes the products obtained:

| Product | % of Total Yield |
|---|---|
| $\phi-\overset{O}{\overset{\|}{C}}-\overset{Br}{\overset{\|}{C}H}-CH_3$ | 20 |
| $\phi-\overset{O}{\overset{\|}{C}}-\overset{Br}{\underset{Br}{\overset{\|}{C}}}-CH_3$ | 80 |

| -continued | |
|---|---|
| Product | % of Total Yield |
| | Total Yield = 19 mg. |

EXAMPLE 9

This example demonstrates the control of the ratio of alpha-halo product to alpha-dihalo product by balancing the level of available alkyne substrate with the level of enzymatic activity. Enzymatic activity is controlled in this example by the availability of hydrogen peroxide.

The procedure of Example 8 was followed except that the pH of the buffer was 6.0 instead of 3.0, and in-situ generation of hydrogen peroxide was made by adding $\mu$-D-glucose (50 mg) and glucose-1-oxidase (0.01 ml) instead of direct addition of $H_2O_2$.

The product ratio obtained was the following:

| Products | % of Total Yield |
|---|---|
| $\phi$-C(=O)-CH(Br)-CH$_3$ | 96 |
| $\phi$-C(=O)-C(Br)(Br)-CH$_3$ | 4 |
| | Total Yield = 3 mg |

EXAMPLE 10

The procedure of Example 1 was followed except acetylene was substituted for methyl acetylene.

One product was detected.

This product had a GC retention time of 5 minutes and showed the mass spectrum diagnostic for bromoacetaldehyde:molecular mass ion at mass 122 and 124 (1:1 in intensity); major fragment mass ions at mass 94 and 96 (1:1 in intensity) from loss of CO from the molecular ion, and at mass 93 and 95 from loss of CHO from the molecular ion.

The following summarizes the results obtained:

| Product | % of Total Yield |
|---|---|
| HC(=O)—CH$_2$Br | ≈100 |
| HC(=O)—CHBr$_2$ | N.D. |
| | Total Yield = 3 mg |

N.D. = Not detected

EXAMPLE 11

The procedure of Example 10 was followed except that potassium iodide was substituted for potassium bromide.

One product was detected.

This product had a GC retention time of 7 minutes and showed the mass spectrum characteristic of iodoacetaldehyde:molecular mass ion at mass 170; major fragment mass ions at mass 142 from loss of CO from the molecular ion, at mass 141 from loss of CHO from the molecular ion, and at mass 127 for I+ ion.

The following summarizes the results obtained:

| Product | % of Total Yield |
|---|---|
| HC(=O)—CH$_2$I | ≈100 |
| HC(=O)—CHI$_2$ | N.D. |
| | Total Yield = 2 mg |

N.D. = Not detected

It may be seen, therefore, that the invention provides an improved process for the manufacture of alpha-halogenated ketones and aldehydes from alkynes. The reaction proceeds enzymatically, does not require the use of free halogen, permits control of the ratio of alpha-halo product to alpha-dihalo product, and offers potential in the effective utilization of coal as a raw feedstock for many industrial processes.

Various modifications of the invention in addition to those described therein will become apparent to those skilled in the art and such are intended to fall within the scope of the appended claims.

What is claimed is:

1. A method for producing alpha halogenated ketones and aldehydes from alkynes, comprising, providing in a reaction vessel a reaction mixture of a haloperoxidase enzyme, an oxidizing agent, and a halide ion source, introducing an alkyne into said reaction vessel, and maintaining said alkyne in contact with said reaction mixture for a sufficient period of time to convert said alkyne to an alpha-halo or alpha-dihalo ketone or aldehyde.

2. A method in accordance with claim 1 wherein said haloperoxidase enzyme is a peroxidase obtained from a member of the group consisting of the microorganism *Caldariomyces fumago*, seaweed, milk, thyroid, leukocytes and horseradish.

3. A method in accordance with claim 1 wherein said oxidizing agent is hydrogen peroxide.

4. A method in accordance with claim 1 wherein said halide ion source is a water soluble halide salt.

5. A method in accordance with claim 1 wherein the reaction is conducted with the pH range of from about 2.2 to about 8.0.

6. A method in accordance with claim 3 wherein said hydrogen peroxide is present in said reaction mixture at a molar ratio to said alkyne of from about 0.5:1 to about 50:1.

7. A method in accordance with claim 3 wherein said hydrogen peroxide is generated in situ.

8. A method in accordance with claim 1 wherein said haloperoxidase is obtained from a member of the group consisting of the microorganism *Caldariomyces fumago*, lactoperoxidase, and sewweed, wherein said oxidizing agent is hydrogen peroxide, wherein said halide ion source is selected from the group consisting of the chloride, bromide and iodidel salts of sodium and potassium, and wherein said reaction takes place in an aqueous environment at ambient conditions of temperature and pressure.

9. A method in accordance with claim 1 wherein said alkyne is selected from the group consisting of: acetylene, methyl acetylene, ethyl acetylene, phenyl acetylene and 1-phenyl-1-propyne.

10. A method in accordance with claim 1 wherein the ratio of alpha-halo to alpha-dihalo product is controlled by selecting a corresponding halide feed.

11. A method in accordance with claim 1 wherein the ratio of alpha-halo to alpha-dihalo product is controlled by balancing the level of available alkyne substrate by controlling the substrate concentration, and by balancing the level of available enzymatic activity by controlling the pH of the reaction mixture or the availability of oxidizing agent.

* * * * *